United States Patent

Imai et al.

[11] Patent Number: 4,557,750
[45] Date of Patent: Dec. 10, 1985

[54] SULFINAMIDE DERIVATIVES, A PROCESS FOR PREPARING THE DERIVATIVES AND HERBICIDES CONTAINING THE SAME

[75] Inventors: Tetsuya Imai; Kenichi Toyohara; Takeshi Goto, all of Naruto; Tadateru Murata, Itano; Akihide Ando; Toshiro Uchida, both of Naruto; Izuru Yamamoto, Setagaya, all of Japan

[73] Assignee: Otsuka Kagaku Yakuhin Kabushiki Kaisha, Osaka, Japan

[21] Appl. No.: 422,910

[22] PCT Filed: Apr. 15, 1982

[86] PCT No.: PCT/JP82/00122
§ 371 Date: Sep. 7, 1982
§ 102(e) Date: Sep. 7, 1982

[51] Int. Cl.$^4$ .................. A01N 57/10; C07C 145/00; C07F 9/02
[52] U.S. Cl. ................................ 71/87; 260/456 NS; 260/940; 260/941
[58] Field of Search ................ 260/456 NS, 940, 941; 71/87

[56] References Cited
FOREIGN PATENT DOCUMENTS
57-99597 6/1982 Japan .................................. 260/940

Primary Examiner—Nicky Chan
Attorney, Agent, or Firm—Larson and Taylor

[57] ABSTRACT

This invention provides sulfinamide derivatives, a process for preparing the derivatives and herbicides containing the same as the active ingredient, the sulfinamide derivatives being represented by the formula

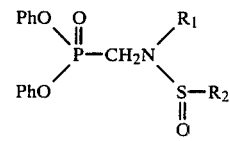

wherein $R_1$ represents an alkoxy ($C_{1-6}$) carbonylmethyl group or cyanomethyl group; $R_2$ represents a group

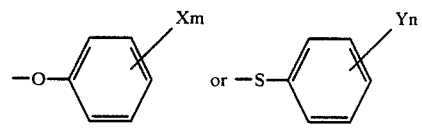

(in which X and Y are each an alkyl group having 1-6 carbon atoms or alkoxy group having 1-6 carbon atoms and m and n are 0 or an integer of 1 to 3); and Ph represents phenyl.

2 Claims, No Drawings

SULFINAMIDE DERIVATIVES, A PROCESS FOR PREPARING THE DERIVATIVES AND HERBICIDES CONTAINING THE SAME

TECHNICAL FIELD

This invention relates to novel sulfinamide derivatives, a process for preparing the derivatives and herbicides containing the same.

BACKGROUND ART

Various types of herbicides have been developed heretofore in the fields of agriculture and horticulture, greatly contributing to the elimination or reduction of weeding work. Among these herbicides, there are known Paraquat (i.e. 1,1'-dimethyl-4,4'-bipyridiniumdichloride) and Glyphosate (i.e., N-phosphonomethylglycine) as useful compounds, particularly as nonselective post-emergence herbicides. However, these conventional herbicides, although markedly effective as herbicides under some conditions, suffer numerous defects when used in some other situations. Thus, it has been desired to provide new herbicides free from such drawbacks. For example, "Paraquat" is a fast-acting contact herbicide, but has herbicidal activity only for a short period of time and high toxicity. "Glyphosate" is a post-emergence translocation herbicide and maintains herbicidal activity for a prolonged period of time. But it has the defects of being slow-active and less effective in killing perennial broad-leaf weeds.

DISCLOSURE OF INVENTION

The sulfinamide derivatives of the present invention are novel compounds heretofore undisclosed in literature and represented by the formula

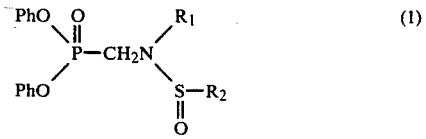

wherein $R_1$ represents an alkoxy ($C_{1-6}$) carbonylmethyl group or cyanomethyl group; $R_2$ represents a group

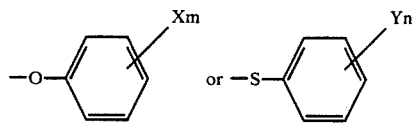

(in which X and Y are each an alkyl group having 1–6 carbon atoms or alkoxy group having 1–6 carbon atoms and m and n are 0 or an integer of 1 to 3); and Ph represents phenyl.

Examples of the alkoxy ($C_{1-6}$) carbonylmethyl groups represented by $R_1$ in the formula 1 previously given are methoxycarbonylmethyl, ethoxycarbonylmethyl, n-propoxycarbonylmethyl, isopropoxycarbonylmethyl, n-butoxycarbonylmethyl, tert-butoxycarbonylmethyl, n-pentyloxycarbonylmethyl, n-hexyloxycarbonylmethyl, etc. Examples of the alkyl groups having 1–6 carbon atoms and represented by X and Y are methyl, ethyl, n-propyl, isopropyl, n-butyl, tert-butyl, n-pentyl, n-hexyl, etc. Examples of the alkoxy groups having 1–6 carbon atoms and represented by X and Y are methoxy, ethoxy, n-propoxy, isopropoxy, n-butoxy, tert-butoxy, n-pentyloxy, n-hexyloxy, etc.

The sulfinamide derivatives of this invention have post-emergence herbicidal activity with foliar application substantially without injury to crop plants such as orange and other fruit trees, mulberry trees, field crop plants, etc. These noxious weeds include, for example, *Panicum crus-galli* L., *Amaranthus retroflexus* L., *Aeschynomene indica*, *Eclipta alba* Hassk, *Digitaria adscendens* Henr. The derivatives of this invention are safely used because of their low toxicity to humans, other animals and fishes.

The sulfinamide derivatives of this invention can be easily prepared by the reactions schematically illustrated below.

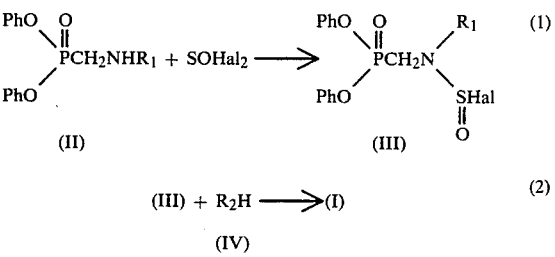

$$(III) + R_2H \longrightarrow (I) \quad (2)$$
$$(IV)$$

In the foregoing equations, $R_1$ and $R_2$ are as defined above, Ph is a phenyl group and Hal is a halogen atom.

Examples of thionyl halides useful in this invention are thionyl chloride, thionyl bromide, etc.

Preferably the reactions of the equations (1) and (2) are carried out after adding to the reaction system a base useful for capturing a hydrogen halide being produced. Examples of solvents to be used in these reactions are diethyl ether, dibutyl ether, tetrahydrofuran, dioxane and like ethers, carbon tetrachloride, chloroform, methylene chloride and like halogenated hydrocarbons, etc. Bases to be used in the reactions include for example triethylamine, tributylamine, dimethylaniline, diethylaniline, N-ethylmorpholine and like tertiary amines, pyridines, etc.

The thionyl halide is used in the reaction of equation (1) in an amount of about 1 to about 1.5 moles, preferably about 1 to about 1.2 moles, per mole of the compound having the formula (II), although the proportions of the two compounds are not particularly limited but can be varied over a wide range. The amount of the base to be used, though nonlimitative and widely variable, is about 1.2 to about 2 moles, preferably about 1.2 to about 1.5 moles, per mole of the compound having the formula (II). The reaction of the equation (1) can be conducted with cooling or at room temperature or increased temperature, usually at a temperature of about −70° to about 50° C., preferably about −10° to about 30° C.

The amounts of the compounds having the formulae (III) and (IV) to be used in the reaction of the equation (2) are not particularly limitative but can be suitably determined over a wide range. The compound of the formula (IV) is used in an amount of usually about 1 to about 1.5 moles, preferably about 1 to about 1.2 moles, per mole of the compound of the formula (III). The amount of the base to be used, though nonlimitative and widely variable, is about 1.2 to about 2 moles, preferably about 1.2 to about 1.5 moles, per mole of the compound having the formula (III). The reaction of the equation (2) can be carried out with cooling or at room temperature or increased temperature, usually at a temperature of about −70° to about 50° C., preferably from about −10° to about 30° C.

The compound of the formula (IV) obtained by the reaction of the equation (1) is usable in the reaction of the equation (2) as isolated from, or as admixed with, the reaction product prepared in the reaction of the equation (1).

Exemplary of the compounds thus prepared according to this invention are as follows.

(N-cyanomethyl-N-diphenylphosphonomethyl)-phenoxysulfinamide,
(N-ethoxycarbonylmethyl-N-diphenylphosphonomethyl)phenoxysulfinamide,
(N-cyanomethyl-N-diphenylphosphonomethyl)(4-methylphenoxy)sulfinamide,
(N-cyanomethyl-N-diphenylphosphonomethyl)(3,4-dimethylphenoxy)sulfinamide,
(N-ethoxycarbonylmethyl-N-diphenylphosphonomethyl)(4-methylphenoxy)sulfinamide,
(N-cyanomethyl-N-diphenylphosphonomethyl)(4-methoxyphenoxy) sulfinamide, and
(N-cyanomethyl-N-diphenylphosphonomethyl)phenylthiosulfinamide.

The herbicides containing the sulfinamide derivative of the formula (I) as the active ingredient are effective in controlling weeds such as *Panicum Crus-galli* L., *Eclipta alba* Hassk, *Amaranthus retroflexus* L., *Aeschynomene indica*, *Digitaria adscendens* Henr, *Eleusine indica* Gaertn., *Alopecurus aequalis* Sobol. var. *amurensis* Ohwi, *Setaria viridis* Beauv, *Polygonum hydropiper* L., *Artemisia vulgaris* L., var. *maximowiczii* Nakai, *Erigeron sumatrensis* Retz, *Rumex japonicus* Houtt., etc. Therefore, the herbicides of this invention are useful in preventing or controlling weeds which are harmful to agricultural crop plants such as orange trees, apple trees or like fruit trees, mulberry trees, tea plants, or which are destruction to the surrounding scenic beauty. The herbicides of the present invention have post-emergence herbicidal activity. They nonselectively act on any of annual and perennial weeds.

The herbicides of this invention are usable for preventing and removing noxious weeds growing in tilled grounds, plantations, mulberry fields, paddy fields before tillage, fallow paddy fields, railroads, levees, parks, etc. The weed killers of this invention are particularly useful for stunting or destroying weeds prior to or after planting crop seeds or before transplanting crop plants. The present herbicides exhibit low toxity to humans, other animals and fishes and thus can be safely used.

When put to use, the sulfinamide derivatives of this invention are applicable singly or in admixture with adjuvants as usually used for preparing agricultural chemicals and are employed in any suitable form, preferably in the form of an emulsion or wettable powder. To ensure stabilized and improved effects of the herbicide, the following adjuvants are usable: diatomaceous earth, kaolin, clay, bentonite and like extenders; dispersions of polyoxyethylenesorbitanmonoolate, sodium dodecylbenzenesulfonate, salt of lignin sulfonic acid and the like; xylol, acetone, methanol, carbon tetrachloride and like organic solvents, etc. In use, the herbicide containing the sulfinamide derivative of this invention as the active ingredient is diluted with water or any other suitable solvent to adjust the concentration of the active ingredient to the desired level, and is applied to the weeds in such a manner as to spread over the entire surfaces of weed stems and leaves. The dilution ratio and amount of the herbicide to be applied are variable and can be suitably determined over a wide range depending on the type of weeds to be controlled, stage of weed growth, shape of the sprayer or like device, the area of the ground for the application, etc. The herbicide is diluted usually to 70 to 1000 folds and applied preferably in an amount of 50 to 200 l/10 a.

The present invention is described below with reference to examples for preparing sulfinamide derivatives of this invention, those for preparing herbicides of this invention and the tests given below.

EXAMPLE 1

Preparation of (N-cyanomethyl-N-diphenylphosphonomethyl)-phenoxysulfinamide

A 6.0 g (0.02 mole) quantity of N-diphenylphosphonomethylaminoacetonitrile, 3.3 ml (0.024 mole) of triethylamine and 50 ml of methylene chloride were cooled to −10° C. To this mixture was added dropwise 2.4 g (0.02 mole) of thionyl chloride. After the addition, the resulting mixture was stirred for 2 hours at room temperature, and was cooled again to −10° C. Thereto was added dropwise a solution of 1.9 g (0.02 mole) of phenol and 3.3 ml (0.024 mole) of triethylamine in 10 ml of methylene chloride. Then the mixture was stirred for 6 hours at room temperature. To the reaction mixture was added 200 ml of methylene chloride, subsequently the resultant admixture was washed with a 5% aqueous solution of NaOH and then with water and dried. The methylene chloride layer was concentrated giving 6.9 g of an oily product. Yield 78.4%. For identification, the oily product was partly purified by silica gel column chromatography using a 4:1 benzene-ethyl acetate as the elution solvent.

The oily product was subjected to NMR in deuteriochloroform with the following results (δ. ppm): 3.94(2H, dd), 4.35(2H, d), 7.04(15H).

Elementary Analysis (as $C_{21}H_{19}N_2O_5PS$):

|  | C | H | N |
| --- | --- | --- | --- |
| Found (%): | 57.14 | 4.29 | 6.19 |
| Calcd. (%): | 57.01 | 4.33 | 6.33 |

As a result, the oily product was identified as a compound represented by the formula.

$$\begin{array}{c} PhO \\ \diagdown \\ \phantom{P}\diagup \\ PhO \end{array} \!\!\!\!\! \begin{array}{c} O \\ \| \\ P-CH_2N \\ \phantom{\|} \end{array} \!\!\!\! \begin{array}{c} CH_2CN \\ \diagup \\ \diagdown \\ SOPh \\ \| \\ O \end{array}$$

EXAMPLE 2

Preparation of (N-ethoxycarbonylmethyl-N-diphenylphosphonomethyl)phenoxysulfinamide Cooled to −10° C. were 7.0 g (0.02 mole) of N-ethoxycarbonylmethyl-N-diphenylphosphonomethylamine, 3.3 ml (0.024 mole) of triethylamine and 50 ml of chloroform. Thereto was added dropwise 2.4 g (0.02 mole) of thionyl chloride. The mixture was stirred for 1 hour at room temperature and was cooled again to −10° C. Thereto was added dropwise a solution of 1.9 g (0.02 mole) of phenol and 3.3 ml (0.024 mole) of triethylamine in 10 ml of chloroform. Subsequently the resulting mixture was agitated at room temperature for 2 hours and left to stand overnight. After the completion of the reaction, 100 ml of chloroform was added to the reaction liquid. Then the mixture was washed with a 5% aqueous solution of NaOH and then with water. The chloroform layer was dried and concentrated, giving 8.0 g of an oily product. Yield 81.6%.

For identification, the oily product was partly purified by silica gel column chromatography using a 4:1 benzene-ethyl acetate mixture as the elution solvent, affording an oily product.

The oily product thus obtained was subjected to NMR in deuteriochloroform with the following results (δ. ppm): 4.20(2H, d), 4.30(2H, s), 4.18(2H, q), 1.20(3H, t), 7.25(15H).

Elementary Analysis (as $C_{23}H_{24}NO_7PS$):

|  | C | H | N |
|---|---|---|---|
| Found (%): | 56.15 | 5.03 | 2.79 |
| Calcd. (%): | 56.44 | 4.94 | 2.86 |

Thus the oily product was identified as a compound represented by the formula

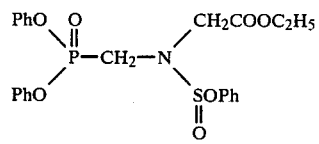

EXAMPLES 3-9

Compounds as shown in Table 1 below were prepared in the same manner as in Example 1. Table 1 indicates the properties of these compounds and the results by NMR.

TABLE 1

| Example | Structure | Property | NMR(in deuterio-chloroform, δ. ppm) |
|---|---|---|---|
| 3 | PhO\P(=O)(/CH2N(CH2COOC2H5)(S(=O)-O-C6H4-CH3))/PhO | Oily | 4.16(2H, d)<br>4.29(2H, s)<br>4.17(2H, q)<br>1.20(3H, t)<br>2.28(3H, s)<br>7.31(14H) |
| 4 | PhO\P(=O)(-CH2N(CH2COOC2H5)(SO2-C6H3(CH3)2))/PhO | Oily | 4.15(2H, d)<br>4.29(2H, s)<br>4.17(2H, q)<br>1.20(3H, t)<br>2.17(6H, s)<br>7.35(13H) |
| 5 | PhO\P(=O)(-CH2N(CH2CN)(SS(=O)-C6H5))/PhO | Oily | 3.80(2H, dd)<br>4.41(2H, d)<br>7.11(15H) |
| 6 | PhO\P(=O)(-CH2N(CH2CN)(SO2-C6H4-CH3))/PhO | Crystal, melting point 44-45° C. | 2.29(3H, s)<br>3.98(2H, dd)<br>4.47(2H, d)<br>7.21(14H) |
| 7 | PhO\P(=O)(-CH2N(CH2CN)(SO2-C6H3(CH3)2))/PhO | Crystal, melting point 55° C. | 2.16(6H, s)<br>4.00(2H, dd)<br>4.44(2H, d)<br>7.22(13H) |
| 8 | PhO\P(=O)(-CH2N(CH2COOCH3)(S(=O)-S-C6H4-OCH3))/PhO | Oily | 4.15(2H, d)<br>4.28(2H, s)<br>3.58(3H, s)<br>3.79(3H, s)<br>7.21(14H) |

TABLE 1-continued

| Example | Structure | Property | NMR(in deuterio-chloroform, δ. ppm) |
|---|---|---|---|
| 9 | PhO\P(=O)(/OPh)—CH2N(\CH2CN)(/O-C6H2(OCH3)3) | Oily | 4.02(2H, dd) 4.45(2H, d) 3.85(3H, s) 3.90(6H, s) 7.15(12H) |

Preparation 1 (30% emulsion)

| | Parts by weight |
|---|---|
| Compound prepared in Example 1 | 30 |
| Polyoxyethylenenonylphenylether | 10 |
| Dimethylsulfoxide | 60 |

The foregoing components were uniformly mixed to prepare an emulsion.

Preparation 2 (50% wettable powder)

| | Parts by weight |
|---|---|
| Compound prepared in Example 2 | 50 |
| Sodium lignin sulfonate | 1 |
| Sodium dodecylbenzenesulfonate | 4 |
| Clay | 45 |

The foregoing components were uniformly mixed and pulverized to prepare wettable powder.

Test 1

(test for herbicidal activity in foliar application)

Wagner pots each having an area of 1/2000 a were filled with alluvial sterilized soil. Then the pots were each planted with one species of seeds of weeds shown in Table 2. When the weeds grew to a specific height (substantially to the 2 or 3 leaf stage), emulsions each containing as the active ingredient respective compounds obtained in Examples 1 to 9 were prepared with the same composition and in the same manner as in Preparation 1 and diluted with water so that the application requires the active ingredient in an amount of 50 g/a. Then the herbicide samples were applied to the weeds in such a manner that the entire surfaces of weed stems and leaves are uniformly covered with the herbicide samples. The herbicidal activity of each sample was evaluated 3 weeks after the application thereof according to the criteria indicated below in which the herbicidal activity thereof is expressed in terms of an index compared with untreated plants. Table 2 shows the results.

| Index | Herbicidal Activity |
|---|---|
| 0 | No change |
| 1 | 1–24%* |
| 2 | 25–49% |
| 3 | 50–74% |
| 4 | 75–99% |
| 5 | Completely killed |

*The percentages in the above table represent a degree of growth inhibition.

TABLE 2

| Test Compounds | Test plants | | | | | | | |
|---|---|---|---|---|---|---|---|---|
| | (A) | (B) | (C) | (D) | (E) | (F) | (G) | (H) |
| Example 1 | 5 | 5 | 4 | 4 | 5 | 5 | 5 | 5 |
| Example 2 | 5 | 4 | 5 | 4 | 5 | 5 | 5 | 5 |
| Example 3 | 5 | 4 | 5 | 4 | 5 | 5 | 5 | 5 |
| Example 4 | 5 | 5 | 5 | 5 | 5 | 5 | 4 | 4 |
| Example 5 | 5 | 5 | 3 | 3 | 4 | 3 | 5 | 3 |
| Example 6 | 5 | 5 | 5 | 4 | 5 | 5 | 4 | 5 |
| Example 7 | 5 | 5 | 5 | 3 | 5 | 5 | 5 | 5 |
| Example 8 | 5 | 5 | 4 | 3 | 5 | 5 | 3 | 4 |
| Example 9 | 5 | 5 | 3 | 3 | 5 | 5 | 4 | 4 |

The names of tests plants (A) to (H) are as follows:
(A) *Eclipta albo* Hassk
(B) *Amaranthus retroflexus* L.
(C) *Aeschynomene indica*
(D) *Panicum crus-galli* L.
(E) *Raphanus sativus* L. var. acanthiformis Makino
(F) *Fagopyrum esculentum* Moench
(G) *Pharbitis Nil* Choisy
(H) *Triticum aestivum* L.

From the results in Table 2, it is seen that the herbicides of this invention exhibit a herbicidal action with post-emergence foliar application. Table 2 is indicative of the results of tests using the plants predominantly comprising annual weeds. An additional test was conducted by employing perennial weeds with similar results. Namely the herbicides of this invention nonselectively acted on the plants.

We claim:

1. Sulfinamide derivative represented by the formula

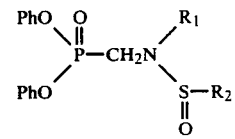

wherein $R_1$ represents an alkoxy ($C_{1-6}$) carbonylmethyl group or cyanomethyl group; $R_2$ represents a group

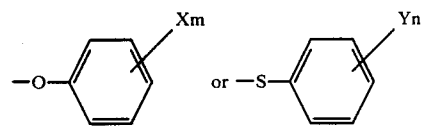

in which X and Y are each an alkyl group having 1–6 carbon atoms or alkoxy group having 1–6 carbon atoms and m and n are 0 or an integer of 1 to 3; and Ph represents phenyl.

2. A herbicide composition containing a diluent and a sulfinamide derivative represented by the formula

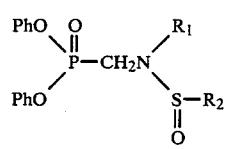
wherein $R_1$ represents alkoxy ($C_{1-6}$) carbonylmethyl group or cyanomethyl group; $R_2$ represents a group
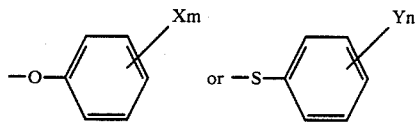
(in which X and Y are each an alkyl group having 1–6 carbon atoms or alkoxy group having 1–6 carbon atoms and m and n are 0 or an integer of 1 to 3); and Ph represents phenyl.
* * * * *